United States Patent
Imbert et al.

(10) Patent No.: US 9,032,802 B2
(45) Date of Patent: May 19, 2015

(54) PHASED ARRAY SYSTEM AND METHOD FOR INSPECTING HELICAL SUBMERGED ARCS WELD (HSAW)

(71) Applicants: Christophe Imbert, St. Augustin de Desmaures (CA); Jinchi Zhang, Quebec (CA); Benoit Lepage, Quebec (CA)

(72) Inventors: Christophe Imbert, St. Augustin de Desmaures (CA); Jinchi Zhang, Quebec (CA); Benoit Lepage, Quebec (CA)

(73) Assignee: OLYMPUS NDT, Waltham, MO (US)

( * ) Notice: Subject to any disclaimer, the term of this patent is extended or adjusted under 35 U.S.C. 154(b) by 357 days.

(21) Appl. No.: 13/750,297

(22) Filed: Jan. 25, 2013

(65) Prior Publication Data

US 2013/0199297 A1 Aug. 8, 2013

Related U.S. Application Data

(60) Provisional application No. 61/590,877, filed on Jan. 26, 2012.

(51) Int. Cl.
*G01N 29/27* (2006.01)
*G01N 29/26* (2006.01)

(52) U.S. Cl.
CPC .............. *G01N 29/27* (2013.01); *G01N 29/262* (2013.01); *G01N 2291/2634* (2013.01); *G01N 2291/2675* (2013.01)

(58) Field of Classification Search
CPC .......... G01N 29/27; G01N 2291/2675; G01N 29/262; G01N 2291/2634
USPC .................................................. 73/629, 622
See application file for complete search history.

(56) References Cited

U.S. PATENT DOCUMENTS

| | | | | |
|---|---|---|---|---|
| 3,868,847 | A | * | 3/1975 | Gunkel ........................... 73/622 |
| 4,351,190 | A | | 9/1982 | Rehme et al. |
| 6,125,705 | A | * | 10/2000 | Johnson ......................... 73/622 |
| 7,044,000 | B2 | * | 5/2006 | Feller ......................... 73/861.27 |
| 8,365,602 | B2 | * | 2/2013 | Imbert et al. ..................... 73/622 |
| 2012/0204645 | A1 | * | 8/2012 | Crumpton et al. .............. 73/588 |
| 2014/0318249 | A1 | * | 10/2014 | S. et al. ........................... 73/588 |

FOREIGN PATENT DOCUMENTS

| | | | |
|---|---|---|---|
| CN | 101300484 | | 11/2008 |
| CN | 102121923 | | 7/2011 |
| WO | WO92/16832 | * | 1/1992 |

OTHER PUBLICATIONS

Office Action issued by Chinese Patent Office on Sep. 29, 2014 in connection with corresponding Chinese Patent Application No. 201310032556.4 and English translation thereof.

\* cited by examiner

*Primary Examiner* — J M Saint Surin
(74) *Attorney, Agent, or Firm* — Ostrolenk Faber LLP

(57) ABSTRACT

A phased array system and the inspection method which is configured to inspect the weld seam of an HSAW for all standard types of flaws located both near pipe's internal and external surfaces in one scan pass, diminishing the need of making mechanical adjustment for the probes during the one pass of scan. The configuration includes the usage of at least one linear PA probe for Lamination inspection right above HAZ zone, at least one pair of PA probes for longitudinal defects inspection and holes detection and at least two pairs of PA probes for transversal defect inspections.

22 Claims, 13 Drawing Sheets

Fig. 5  Pitch-Catch Configuration

PHASED ARRAY SYSTEM AND METHOD FOR INSPECTING HELICAL SUBMERGED ARCS WELD (HSAW)

CROSS-REFERENCE TO RELATED APPLICATIONS

This application claims the benefit and priority of U.S. Provisional patent application Ser. No. 61,590,877 filed Jan. 26, 2012 entitled A PHASED ARRAY SYSTEM FOR INSPECTING HELLICAL SUBMERGED ARCS, the entire disclosure of which is incorporated herein by reference.

FIELD OF THE INVENTION

The present disclosure generally relates to a method and a system for inspecting flaws in test objects using phased array ultrasonic systems and, more particularly, to a phased array system devised to inspect helical submerged arc welds (HSAW).

BACKGROUND

The Submerged Arc Welding Process

The Submerged Arc Welding (SAW) process is a method of electrical fusion welding performed with a concealed arc. In contrast to arc welding with welding electrodes, the arc in this case is hidden from view and burns under a blanket of slag and flux. One of the characteristic features of Submerged Arc Weld (SAW) is its high deposition rate, which essentially stems from the high current strength which is applied combined with favorable heat balance. This deposit, as is also called weld bead, is an obstacle to the inspection since it forms a protrusion that creates mechanical constraints for the water wedges positioning.

Helical Submerged Arc Welding (herein later as HSAW) is one type of SAW process and is commonly used in steel industry for many applications including joining hot rolled coil (of various widths) creating a helical seam around the finished pipe. SAW or Submerged Arc Welding means the electrode used to join the coil edges is submerged in flux to protect the weld pool from contamination. HSAW and LSAW (Longitudinal Submerged Arc Weld) pipes are used as Line Pipes for Oil and Gas transportation. HSAW is also commonly used in water transportation.

HSAW pipes are large in diameter size, ranging from 16" to 100" with a maximum thickness of 25 mm (1 inch).

Weld seam angles vary and are function of the coil width and pipe diameter. The range of the weld seam angles is approximately from 51 to 75 degrees. There are also different types of weld seams that require different types of inspection solutions. The weld seam angles are key-parameters for the suggested solution as it defines directly the oblique orientation of the Longitudinal and Transversal defects.

Prediction of the weld bead width and reinforcement is the subject of advanced research in metallographic and welding process; there are no simple formulae to evaluate these parameters. The integrated forming of SAW welding line can be regarded as part of the functions of conventional spiral pipe manufacturing facility. This type of manufacturing process requires an in-line inspection configuration where the pipe length is infinite and the inspection data storage needs to be synchronized with the moving saw.

Facilities with separate forming and SAW welding line with a manufacturing process requires an off-line inspection configuration where the pipe length is finite and known prior to the inspection.

Existing Test Method for Ultrasonic Inspection of Welded Pipe

For weld inspection in pipes, the cross-section to be tested is reduced to the weld seam itself and to the Heat-Affected Zones (HAZ) abutting the weld. The welding process is already automated in order to make an automated testing system worthwhile.

The common existing inspection and measurements tasks performed by a group or array of single or dual-element probes ultrasonic probes (UT probes) to inspect the defects are as follows.

i. Longitudinal defects, including internal (LID) and external (LOD) notches, through-hole defects (TDH);
ii. Longitudinal defect of mid-seam mid-wall flat-bottom hole (MWFBH);
iii. Transverse defects (internal and external notches or "T ID and T OD in short form, respectively);
iv. Lamination testing within the Heat-affected Zone (HAZ);
v. Wall Thickness Measurement in HAZ.

Inspection standards typically require the detection of the reference defect from multiple directions. As defined in inspection standard "DNV-OSOF101 APPENDIX D" (paragraph 1311, 1312 and 1313, later as "Standard"), it is required to use opposing probe configuration (from each side of the weld). Opposing probe configuration for HSAW welds longitudinal defects are referred to as forward (FW) and backward (BW) while opposite probe configuration for HSAW welds for transversal defects are referred to as clockwise (CW) and counterclockwise (CCW).

With the conventional existing techniques using UT to inspect HSAW, each test of the above listed requires a respective and substantially accurate incidence angle. Longitudinal probe pairs, sometimes tandem probes, transverse and lamination probes are supplied. This quickly results in a testing system with a multitude of electronic channels and probes.

It is known that in order to achieve to above tasks, in existing practice using UT probes to perform the inspection, at least four groups with a total number of at least 18 are required. More should be noted that it is not just the large number of probes involved in the existing practice, each of those pairs of probes need accurate mechanical adjustment with respect of the tube diameter and thickness for the inspection to be reliable. The requirement of such constant adjustment largely impedes the production rate. Otherwise the reliability of the inspection suffers.

Since the testing mechanics has to be adjustable in accordance to the weld angle and space is rather limited when more than four probe pairs is required, a second round of weld testing mechanics and a second machine stand are often needed.

In addition, the use of UT probe pairs centered with respect to the weld allow for the detection of typical defects within the weld and also for using the through-transmission signal for constant coupling check between the two probes. If the V-transmission signal is missing or weakened, the culprit is either due to the coupling, the probe(s) or the entire system that is not working correctly. Thus, the transmission signal is constantly supervised to ensure a stable operation of the system. If the typical ultrasonic beam cannot cover the entire wall thickness, more than one probe pair has to be used.

Existing effort has been seen in patents U.S. Pat. Nos. 3,552,191, 3,868,847 and 4,131,026, each of which provides improvement to the system or method of using conventional single element or dual element UT probes to perform the inspection delineated above. US U.S. Pat. No. 3,552,191 uses ultrasound probes to inspect some regions of an HSAW with a flat (non-curved) layout by mechanically moving the probes. Both U.S. Pat. Nos. 3,868,847 and 4,131,026 uses a series of fixed transducers (UT) in different operating modes to scan a longitudinal weld line.

U.S. Pat. No. 5,583,292 teaches the usage of phased array technology for weld line inspection. However, it does weld line inspection by measuring the wall thickness of a weld line. It does not address full-weld width inspection for all range of flaws along a helical weld line, as required in the Standard. The contents of the aforementioned U.S. patents are incorporated by reference herein.

The weld inspection requires a smooth helical pipe movement with respect to the probes, making the seam tracking an essential but difficult task.

SUMMARY

Accordingly, it is a general object of the present disclosure to provide a phased array system and the inspection method which is configured in a non-conventional way by which the weld seam of an HSAW can be inspected for all standard types of flaws located both near pipe's internal and external surfaces in one pass, diminishing the need of making mechanical adjustment for the probes during the one pass of scan.

The above objective is achieved preferably by using seven linear PA probes aligned with the pipe generatrix in the following manner:

One for Lamination inspection right above the Heat Affected Zone (HAZ). HAZ is commonly known and not show specifically in the drawings of the present disclosure;

Two pairs of PA probes for longitudinal defects inspection and holes detection, which are conventionally achieved by using UT probes performing forward (FW) and backward (BW) inspections.

Two pairs of PA probes for transversal defect inspections which are conventionally achieved by using UT probes making clockwise (CW) and counter-clockwise (CCW) directions.

It is another object of the present disclosure to provide a PA system to inspect all typical flaws in HSAW, diminishing the need for mechanical probe adjustments while accommodating a large range of pipe wall thickness.

It is another object of the present disclosure to provide a PA system to inspect all typical flaws in HSAW, by using a novel combination of PA probes' mechanical angles, focal laws, special sound paths and approximation technique.

Inspection methods, where the wear plates used to adapt the water wedge to the pipe diameter, have only one radius of curvature.

It is yet another object of the present disclosure to provide a PA system to inspect longitudinal flaw inspections, wherein the internal and external notches inspection is achievable from only one side of flaw with only one probe.

It is another object of the present disclosure to provide a PA system to inspect longitudinal flaws, wherein a tandem method is employed within a two different aperture of a single PA probe, which could be used independently for both in-line or off-line inspection.

It is another object of the present disclosure to provide a PA system to inspect transversal flaws, wherein the internal and external notch inspection can be achieved by placing only one pair of probes on the external notch side working in pitch-catch mode.

Yet another object of the present disclosure is to provide a PA inspection method wherein coupling check is employed which has not seen to be used for phased array system in the existing practice.

DESCRIPTION OF THE PREFERRED EMBODIMENT

The preferred embodiment according to the present disclosure comprises usage of one or more phased array acquisition systems, using a plurality of phase array probes and employing layout of phased array probes and the corresponding scanning focal laws to achieve complete in-line inspection on HSAW.

The usage of short forms follows the industry convention. The following nomenclature should be noted in order to assist the reading for the present disclosure.

P-C: pitch-catch mode;
P-E: pulse-echo mode;
ID and OD: inside diameter and outside diameter, respectively;
MW FBH: mid-wall flat bottom holes;
TDH: thru-drill-holes;
TOF: time-of-flight;
FW and BW: inspections in forward and backward directions to cover both sides of the defects (notches);
CC and CCW: inspections in clockwise and counter-clockwise directions in existing practice, to cover both sides of the defects.

Figure 1:
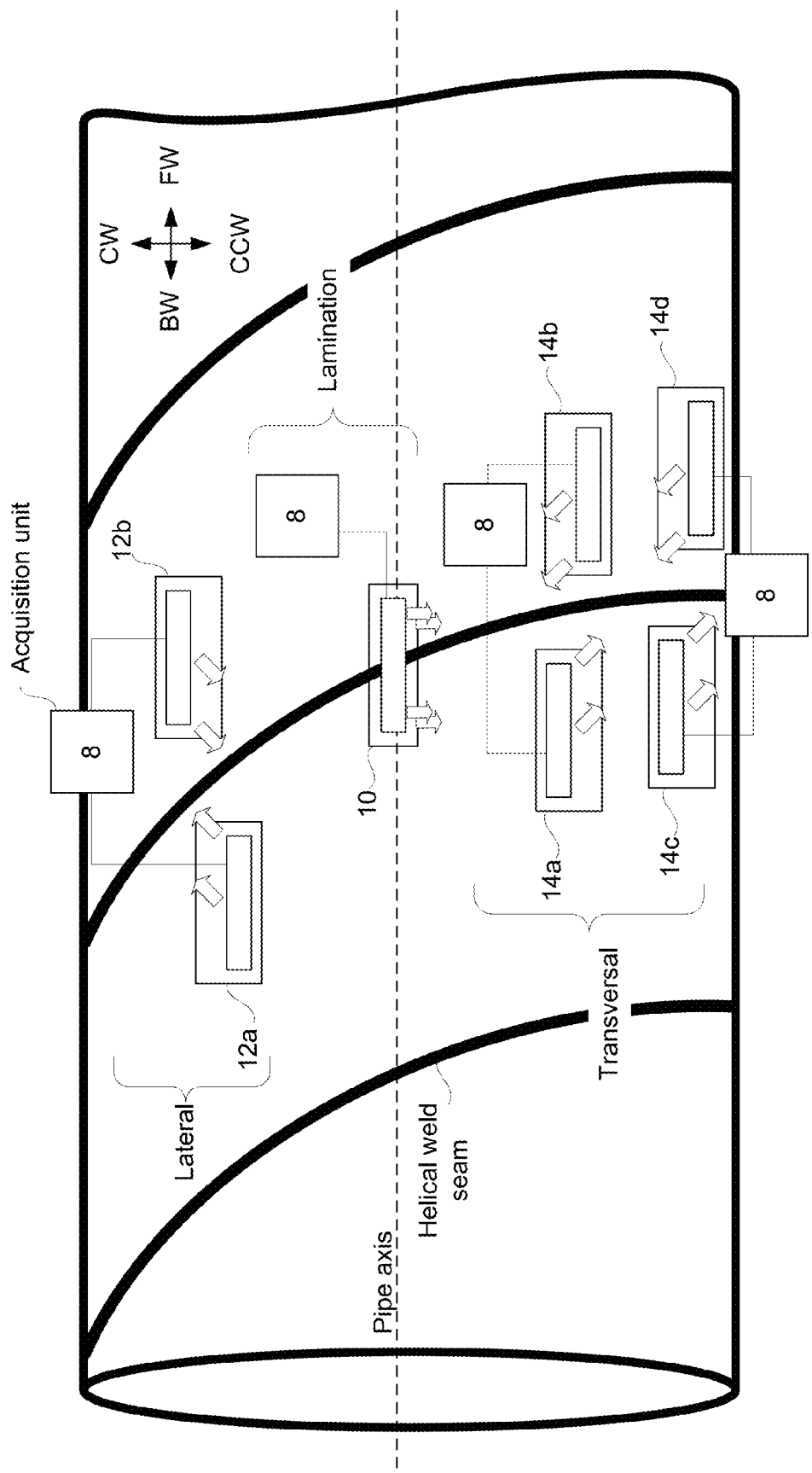
FIG. 1 is a schematic view of the configuration of all PA probes devised in the phased array HSAW system in order to achieve a full scan in one pass according to the present disclosure.

The preferred embodiment of the present disclosure is provided in reference to FIG. 1, wherein a PA system configured is used to cover all of the defects listed in the aforementioned Background section in one pass of the pipe scan, using the minimum number of probes with the least amount of mechanical adjustment need during a scan session.

It should be noted that FIG. 1 illustrates an exemplary case wherein all of the possible defects listed in the BACKGROUND section is intended to be inspected. It should be understood that inspection configuration can alter based on different types of defects are intended to be cover; such alternation is within the scope and teaching of the present disclosure.

Still referring to FIG. 1, the exemplary arrangement of PA probes according to the present disclosure includes three different layers of probes as follows.

Layer 1, identifiable as probe 10, is used to inspect the Heat Affected Zone (on or around the seam line, later as HAZ) for Lamination defect. During the inspection, probes move relatively to the pipe helically, always on top of the seam line, wherein probes remains fixed no matter what the weld seam angle is. It should be noted that it is beneficial to place the others layers of probes as close as possible to the top generatrix to reduce the effects weld seam angle variations. Details of probe 10 are provided in FIGS. 1 and 8.

Layer 2, identifiable as probes 12a and 12b symmetrically arranged with respect to one generatrix (close to the top generatrix) to detect the Longitudinal notches, Thru Drill Hole and mid-wall flat-bottom-hole (MW FBH), in both forward (later FW) and backward (later BW) directions in one pass of scan. Details are given in FIGS. 1, 2 and 3.

Layer 3, identifiable as a first pair of probes 14a and 14b and a second pair of probe 14c and 14d with each pair symmetrically arranged with respect to one generatrix (close to the top generatrix) to detect the Transversal notches in CW and CCW directions. Details are given in FIGS. 1 and 4 through 7.

As can be seen in FIG. 1, this configuration requires only seven linear phased array probes to perform the tasks that otherwise require 18 conventional UT probes with the prior art solutions. More importantly, the present configuration diminishes the need of constantly adjusting the probes due to the combination usage of mechanical angles, aperture pairing, aperture scanning and electronic angles automatically, details of which are provided in the subsequent description.

It should also be noted that associated with this exemplary PA probe configuration, each water wedge axis is always parallel to one generatrix of the pipe. In this way, a commonly used wear plate with only one radius of curvature is needed. Locating water wedge according to the generatrix is advantageous since it is much simpler and more efficient than locating the water wedge using helical weld seam as reference, which is the case of the conventional inspection configuration. In that case, a wear plate with complex shape with two radius of curvature or water squirted probes are required.

Figure 2:
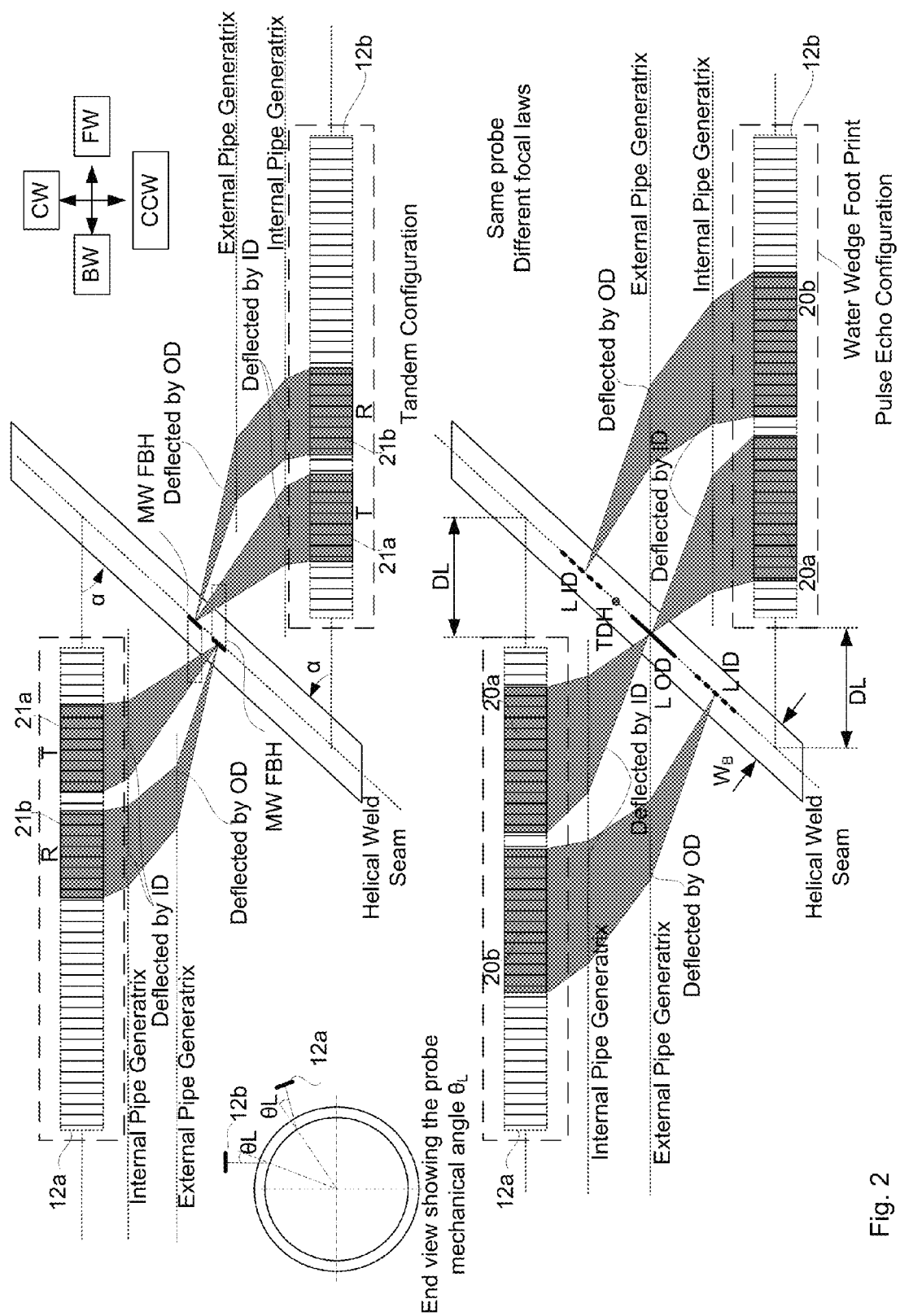
FIG. 2 is a schematic view of a pair of the PA probes for longitudinal flaw detections shown in FIG. 1.

As shown in the exemplary configuration of PA probes in FIG. 1, the PA probes are linear and always mounted parallel to the pipe generatrix. For the configuration of longitudinal flaw detections and that of transversal flaw detections, the right beam angle for each reference defect is obtained by a combination of one mechanical angle given by the probe holder and one electronic angle controlled by the focal laws applied on the PA probes during inspection (the mechanical angle is shown in FIG. 2). For the longitudinal flaw detections, the electronically-controlled steering angle and the electronically-controlled aperture translation along probe provide two available freedoms for canceling mechanic adjustments of probe positions when the pipe wall thickness or weld seam angle changes. For the transversal flaw detections, a pair of probes in P-C mode allows a linear scan across the weld seam width, without frequent mechanic adjustment needed. The efficiency in adjustment of focal laws in each PA probe lifts the burden of making mechanical adjustment or using beam-spread probes as it is required in existing UT operations.

It should be appreciated that the above layout shown in FIG. 1 makes full usage of the advantage PA probe provides, that is the width of the scanning coverage can accommodate small variation of weld seam position and avoid a costly and complex weld tracking system as required by conventional UT techniques described in the BACKGROUND.

Inspection Method for Longitudinal Notches, TDH and MW FBH

Figure 3:
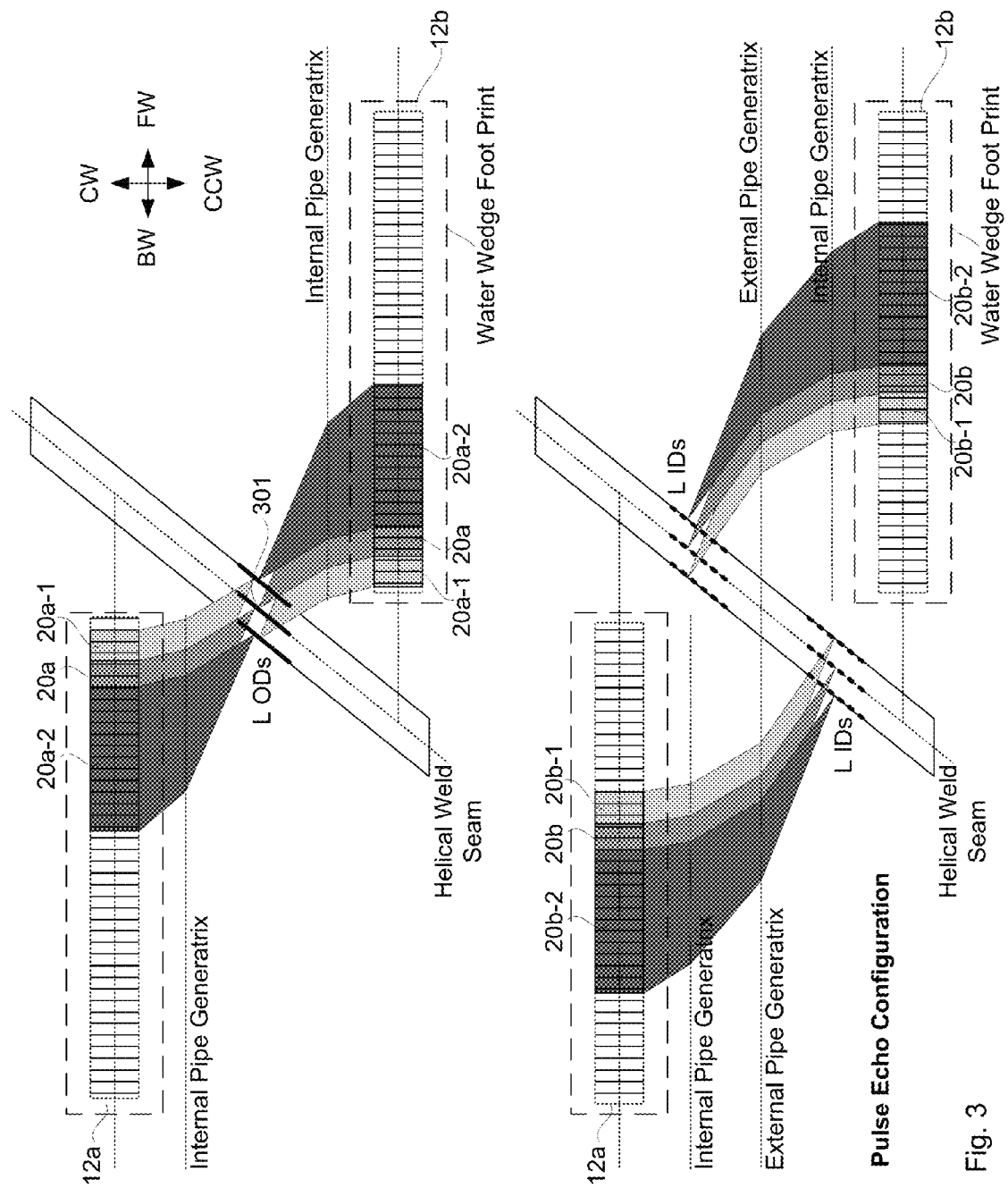
FIG. 3 is a schematic view of the linear scan across the weld seam with the PA probes for longitudinal ID and OD notch detections.

As seen in FIGS. 2 and 3, the Longitudinal PA probes 12a and 12b, respectively for the inspections otherwise carried by existing practice in the FW and BW directions, are mounted parallel to the pipe axis, and the probe axis forms an angle α with respect to the axis of the helical weld seam. As mounted in the probe holder, each PA probe is mechanically tilted of an angle $\theta_L$ with the normal of the natural beam exit point on the pipe surface. Then, an electronic steering angle $\beta_L$ (not shown but commonly known by those skilled in the art) is generated to detect a notch oriented at α angle. The steering angle $\beta_L$ is the same when used for inspection of internal and external diameter surfaces.

As shown in FIG. 2, the position of the first aperture 20a, on the linear PA probe 12a, is related to the detection of the external (OD) longitudinal notch L OD located on the center on the weld seam bead. The distance from the first element of the first aperture 20a to the weld seam center is a function of the pipe wall thickness and the inspection angle applied in the operation (the distance changes very little versus the pipe diameter since the pipe diameter is generally relative large). Aperture 20b is related to the detection of the internal longitudinal notch L ID that uses one more leg of sound beam than the aperture 20a does.

The distance between the probe or more precisely the Water Wedge flank and the center of the weld seam, named $D_L$ in the FIG. 2, is computed in order to maintain an acceptable detection performance and avoid mechanical interference between the Water Wedge and the weld bead.

In the optimization of the distance DL, the weld seam angle α is considered. The method as presently disclosed aims to maintain water wedge at a fixed position independently of the weld seam angle and independently to the wall thickness.

Referring to FIG. 2, distance $D_L$ is determined by combined factors of the following:

the minimum wall thickness of the pipe $WT_{min}$, wherein WT denotes to wall thickness,
the water wedge angle $\theta_L$,
the weld seam angle α,
the weld seam bead width $W_B$.

Figure 9:
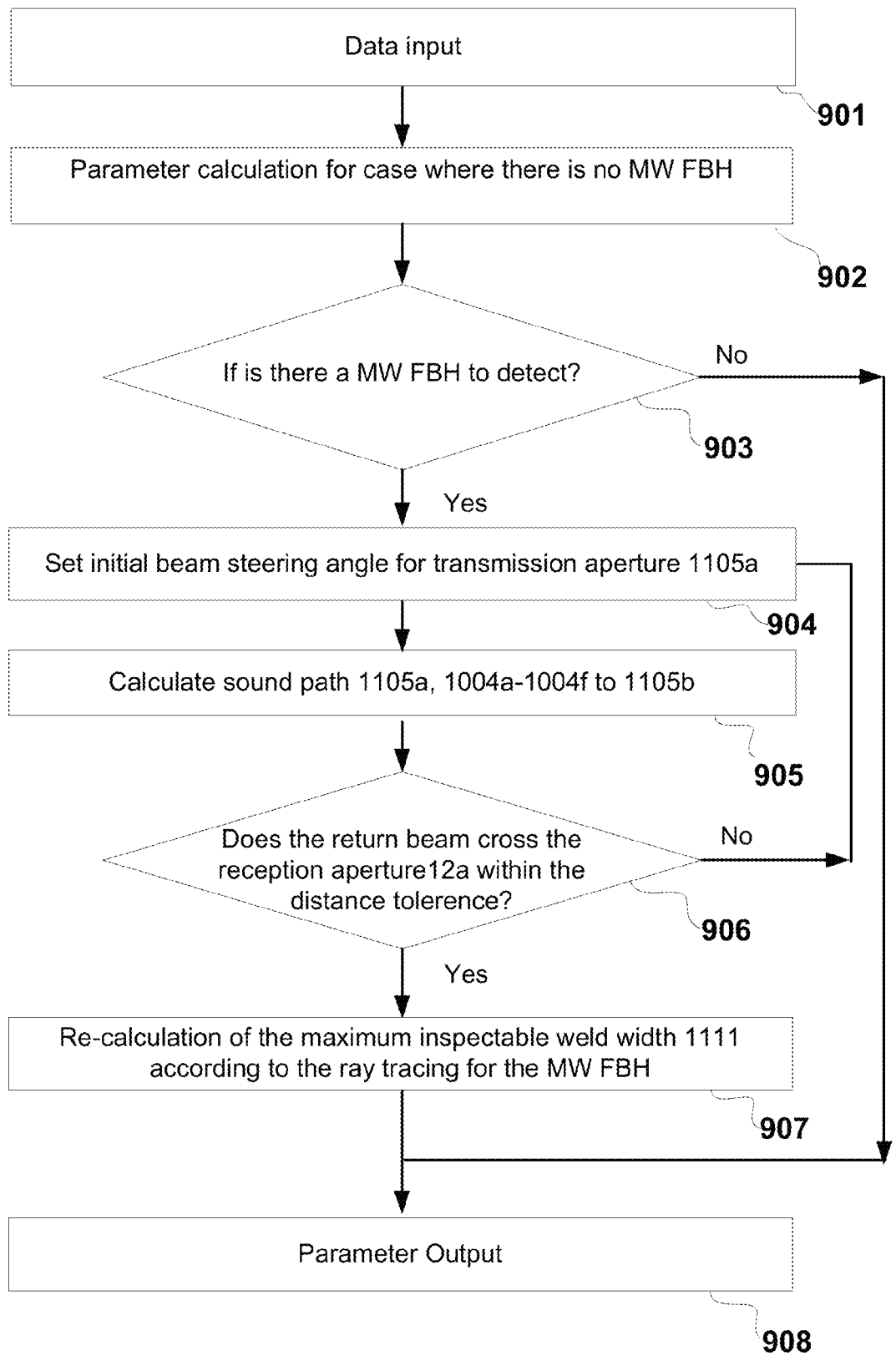
FIG. 9 is a flow chart of the ray tracing for the longitudinal flaw detections shown in FIGS. 2 and 3.
Figure 10:
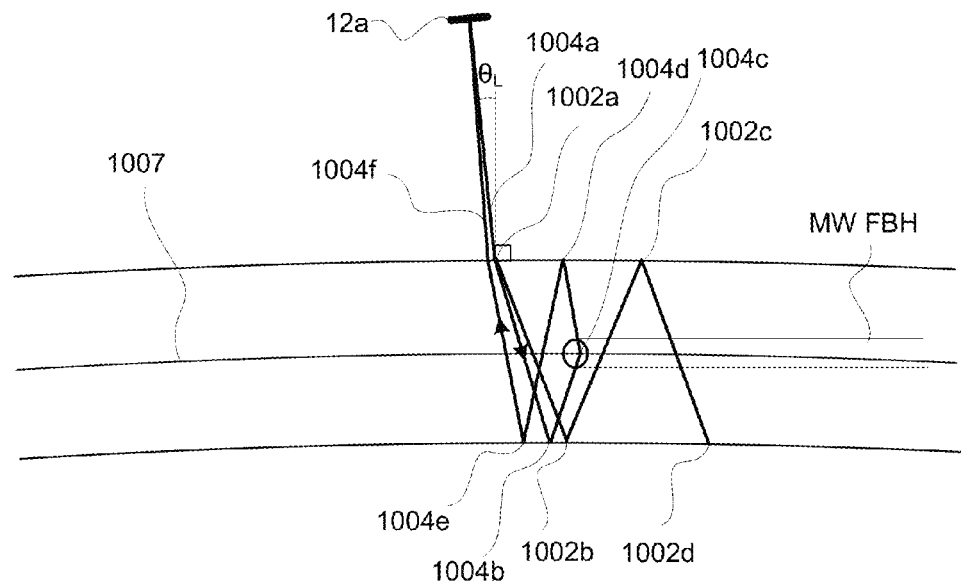
FIG. 10 is an end view of an exemplary ray tracing for the longitudinal flaw detections shown by FIGS. 2 and 3.
Figure 11:
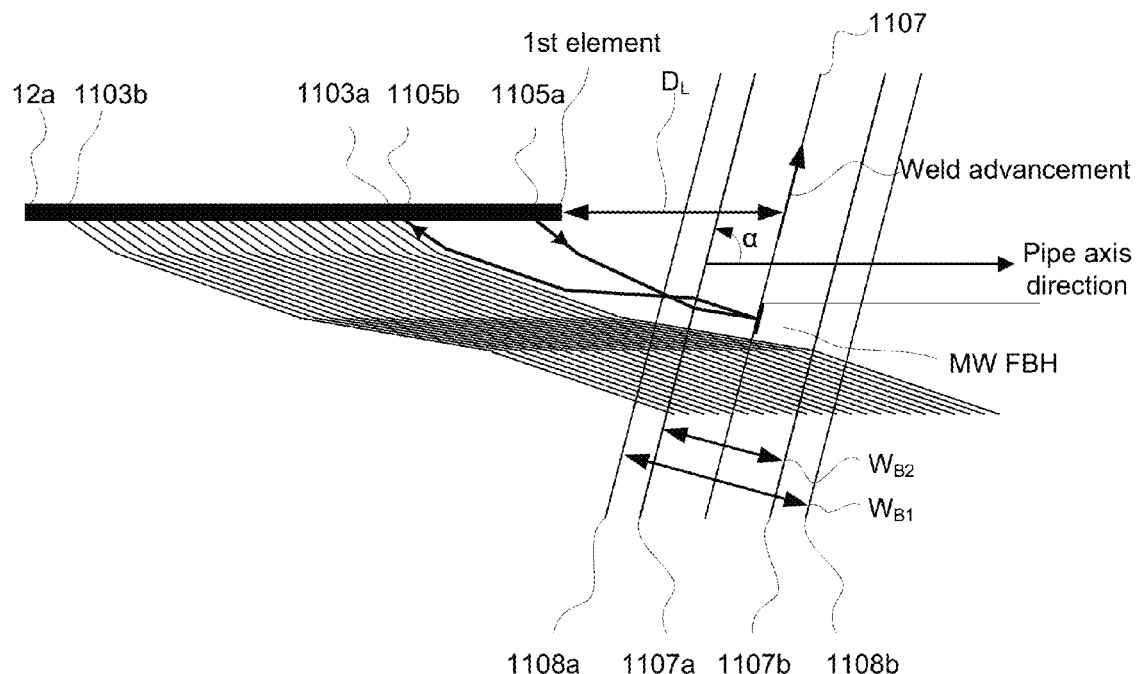
FIG. 11 is a top view of an exemplary ray tracing for the longitudinal flaw detections shown by FIGS. 2 and 3.

Detailed steps of achieving for each batch of inspection $D_L$ are further provided in descriptions associated with FIGS. 9, 10 and 11.

It should be noted that as described in the BACKGROUND in the preceding section regarding the SAW welding process, a deposit resulting in a large weld bead is often made during the welding. The width of the weld bead is a function of the wall thickness of the pipe. Therefore, it could be necessary to consider two or several probe positions to cover a large range of wall thickness prior to inspections. In this case, we will have an optimized distance $D_L$ for a given range of wall thickness.

The detection of the thru-drilled-holes (TDH) as shown in FIG. 2 is similar to the inspection of the longitudinal OD (L OD) notch and longitudinal ID notch (L ID).

It can be appreciated that for MW FBH, a tandem configuration composed of apertures 21a (or transmitter T) and 21b (or receptor R) can be implemented directly with the PA probe used for longitudinal flaw detection as shown in FIG. 2. In this case, the goal is to compute the Emitting and Receiving apertures position as a function of the wall thickness and the weld seam angle α. More details are shown in illustration in FIG. 3.

Reference is now moved onto FIG. 3. Coupling check can be done with probes 12a and 12b by steering the beam on the pipe OD at a location with equal distances from the two probes, firing the first probe and monitoring the signal received on the predicted aperture of the second probe. This coupling check technique is similar to that of the X configuration used in the conventional UT HSAW systems. Even better, the middle skip point 301 of the two opposite apertures 20a-20a respectively in probes 12a and 12b could be displaced away from the weld zone to have a weld geometry-independent signal. The coupling check can be done in an independent channel, where the transmitter aperture and receiver aperture in the opposite probes are paired to work together.

Selection of different apertures (or aperture positions) on the PA probe allows detection of external notches L ODs by apertures scanning from 20a-1, 20a to 20a-2, or internal notches L IDs by further aperture scanning from 20b-1, 20b to 20b-2 in one pass of scan. It can be noted that in this arrangement, apertures 20a group is closer than apertures in 20b group. The weld seam coverage is thus obtained by aperture scanning across the weld width as shown in FIG. 3.

Inspection Method for Transversal Flaws Using Pitch-Catch Mode

Figure 4:
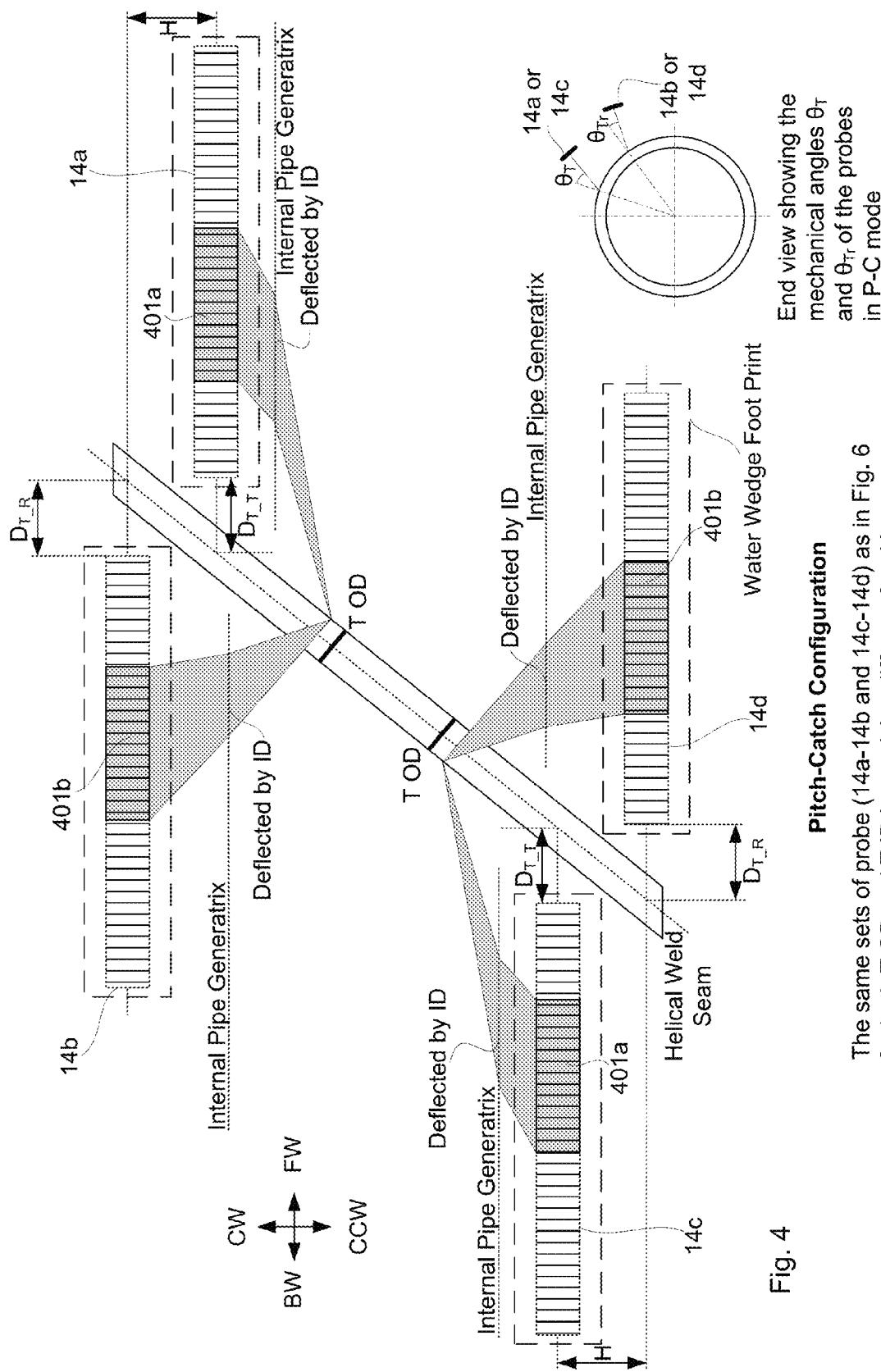
FIG. 4 is a schematic view of two pairs of PA probes in P-C mode.

Referring to FIG. 4, the transversal PA probes are also mounted in parallel to the pipe generatrix. The probe axis makes an angle α with respect to the axis of the helical weld seam. A pair of probes composed of a transmitter 14a and a receiver 14b forms a pitch-catch configuration that scans the weld seam in the CCW direction. As mounted in the probe holder, the PA probes are respectively mechanically tilted of an angle to the normal of the natural beam exit point on the pipe surface. The tilted angles are named $\theta_T$ and $\theta_{Tr}$ as shown in FIG. 4 for probes 14a and 14c, or 14b and 14d, respectively. These angles are also called mechanical angles.

It should be noted that mechanical angles in normal conventional phased array operations are usually kept around zero, meaning phased array probes are conventionally place normal to its inspection surfaces. However, consist and significantly larger than zero mechanical angles are herein used, in combination with steering angles to achieve the inspection tasks in the present disclosure.

Then, an electronic beam steering of the two apertures 401a and 401b respectively at angles $\beta_{T\_OD}$ and $\beta_{Tr\_OD}$ (not shown but commonly known by those skilled in the art) is generated to detect in pitch-catch mode the external notch T OD.

Figure 6:
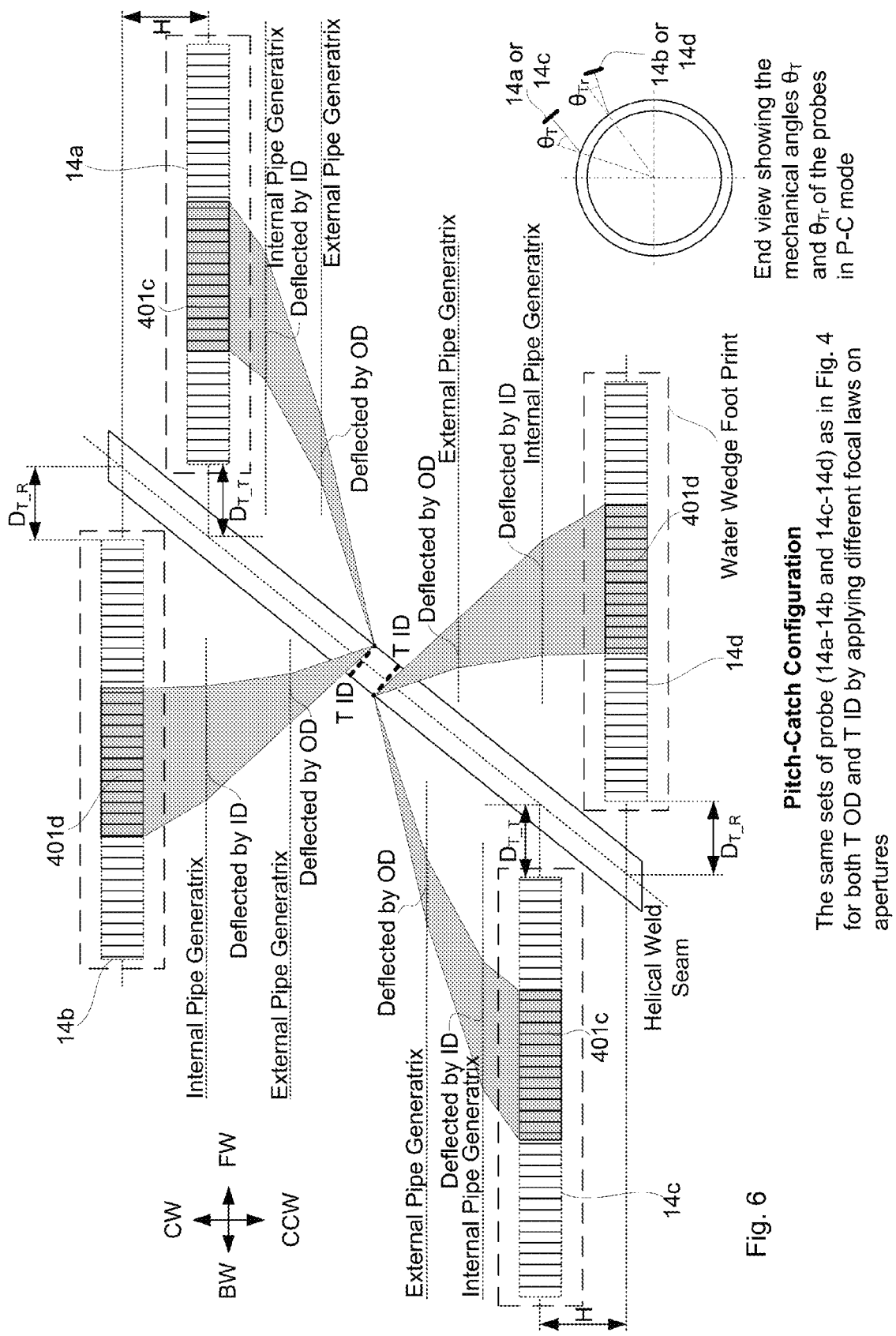
FIG. 6 is a detailed schematic view of two pairs of PA probes in P-C mode.

Referring now to FIG. 6, with the same pair of probes, an electronic beam steering of the two apertures 401c and 401d respectively at angles at $\beta_{T\_ID}$ and $\beta_{T\_ID}$ (not shown but commonly known by those skilled in the art) is generated to detect the internal notch T ID.

As shown in FIGS. 4 and 6, both the external and internal notches are oriented at α+π/2 angle. The distance between the first element of each probe and the weld center is named $D_T$ or $D_{T\_R}$, respectively for the transmitter probes and receiver probes. The circumferential separation between a pair of two probe centers is named H.

As shown in FIG. 4, the pitch-catch sound path starting from transmitter aperture 401a and arriving at receiver aperture 401b detects the external notch T OD at the right edge of the weld seam; similarly, as shown in FIG. 6, with the same pair of probes, the pitch-catch sound path starting from transmitter aperture 401c and arriving at receiver aperture 401d detects the internal notch T ID at the right edge of the weld seam. The distinction of the detections of notch T OD and notch T ID is controlled by different focal laws, that is, the electric steering angles $\beta_{T\_OD}$ and $\beta_{T\_ID}$, $\beta_{Tr\_OD}$ and $\beta_{Tr\_ID}$ are different, the positions of apertures 401a and 401c are different, as well as the positions of apertures 401b and 401d are different.

Figure 5:
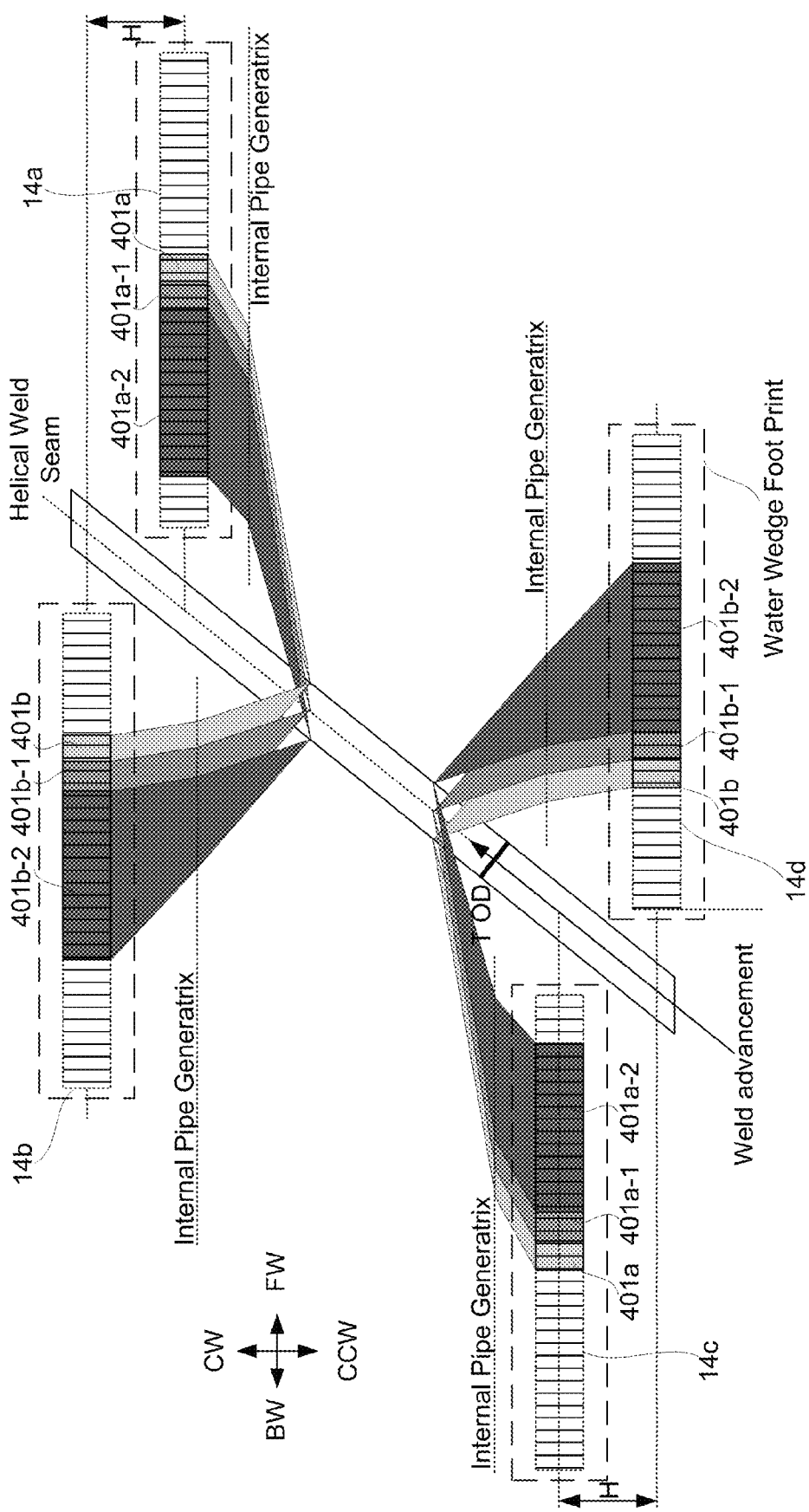
FIG. 5 is a schematic view of the linear scan across the weld seam with two pairs of PA probes in P-C mode for transversal OD notches detection.

Referring to FIG. 5, probe pair 14a and 14b are used to perform aperture scans with P-C mode. For P-C mode, aperture pairs are 401a and 401b, 401a-1 and 401b-1 and 401a-2 and 401b-2 are used to cover the whole weld seam from the right edge to the left edge. As the weld seam advances, notch T OD is scanned across notch length (the inspection points are parallel to pipe generatrix). The aperture scanning allows the coverage of full weld width and full weld thickness. The aperture scanning allows the coverage of full weld width and full weld thickness.

Figure 7:
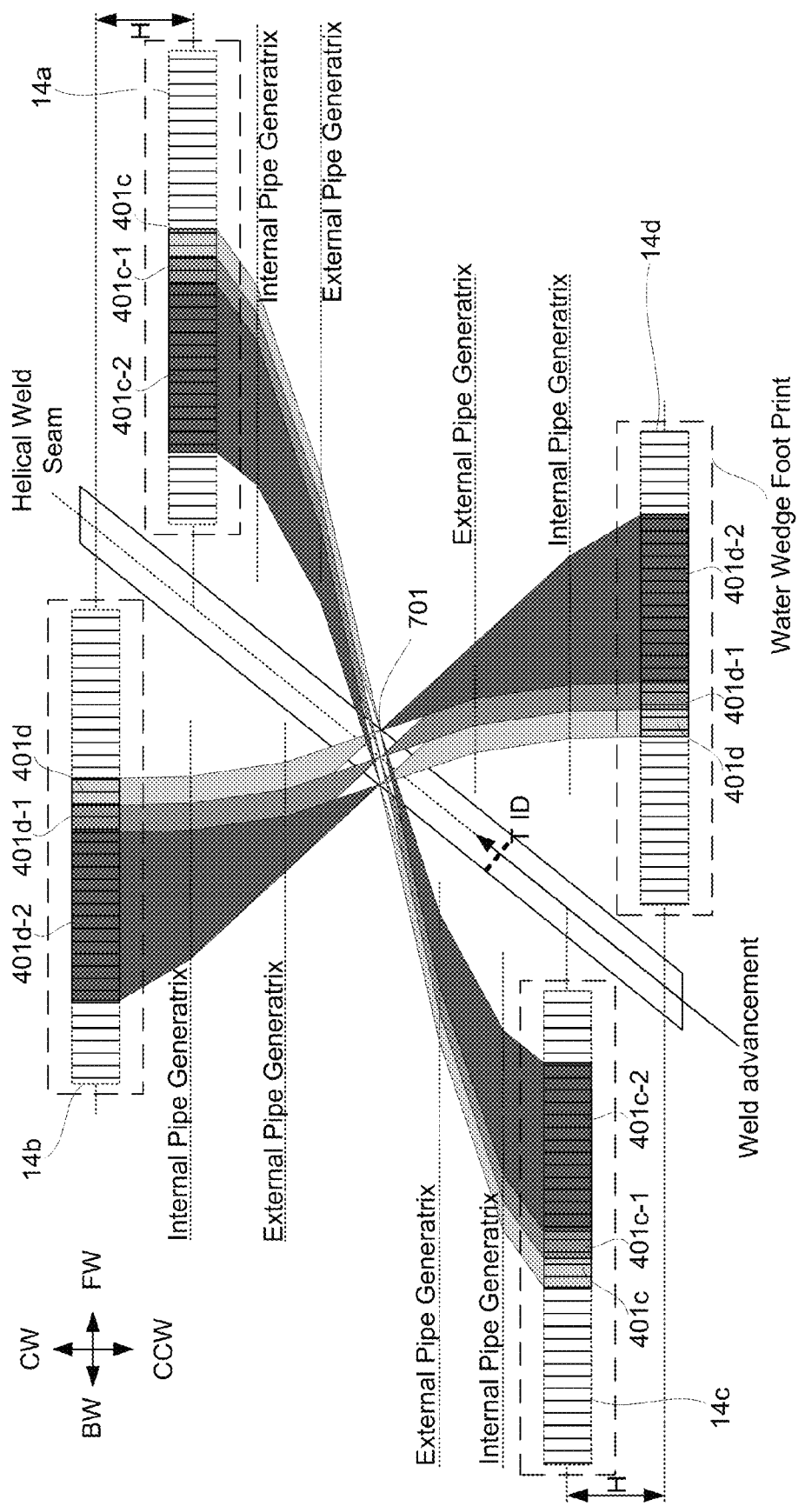
FIG. 7 is a more detailed schematic view of the linear scan across the weld seam with two pairs of PA probes in P-C mode for transversal ID notches detection.

Similarly as shown in FIG. 7, notch T ID is scanned by aperture pairs from 401c and 401d to that of 401c-2 and 401d-2. The aperture scanning allows the coverage of full weld width and full weld thickness.

As can be noted, similarly, a second pair of probes 14c and 14d should be used for the transversal OD and ID notch inspections in the CW direction, as shown in FIGS. 4 to 7.

It should be noted that, because of the use of P-C mode, the circumferential positions of pairs of probes 14a and probe 14b or 14c and 14d have to change when the weld angle or the wall thickness changes. This occurs during the change among different batches of pipe being inspected. Distances $D_{T\_T}$ and $D_{T\_R}$ should change either when there is a geometric interference between a water wedge foot print and the weld seam, or when a probe is too far from the weld. These values could be influenced by the changes of the wall thickness and the weld angle, but, with the help of aperture scanning, only a few discrete values are necessary to adapt to those pipe parameter changes. The advantages of the disclosed P-C mode over the conventional ones that use UT or phased-array techniques are as follows.

The linear scan of the P-C configuration covers the full width of weld seam largely without mechanical adjustment; while the width coverage done by the linear scan rather than by a spread beam used in conventional UT improves the signal-to-noise ratio. The refraction angle of the linear scan is constant, providing consistent echo signals across the weld width.

With the flexibility of the beam steering and aperture scanning, both the external transversal notch and the internal transversal notch are scanned with one pair of probes (in CW or CCW direction). This feature saves the probe quantity.

Referring to FIG. 7, similarly, a coupling check can be done with a probe pair 14a and 14c or 14b and 14d by steering the beam on the pipe ID using a first probe of the first pair such that the reflected beam is received on the second probe at a predefined aperture. This coupling check technique is similar to that of the X configuration used in the conventional HSAW systems. More advantageously, the middle skip point of the two opposite apertures could be displaced away from the weld zone to have a weld geometry-independent signal. For example, by moving aperture positions, the middle skip point 701 of the aperture 401*d* in probe 14*b* and the aperture 401*d*-2 in probe 14d could be displaced to the right from its current position. The coupling check can be done in an independent channel, where the transmitter aperture and the receiver aperture respectively in a pair of opposite probes work together.

Inspection Method for Lamination Defects

Figure 8:
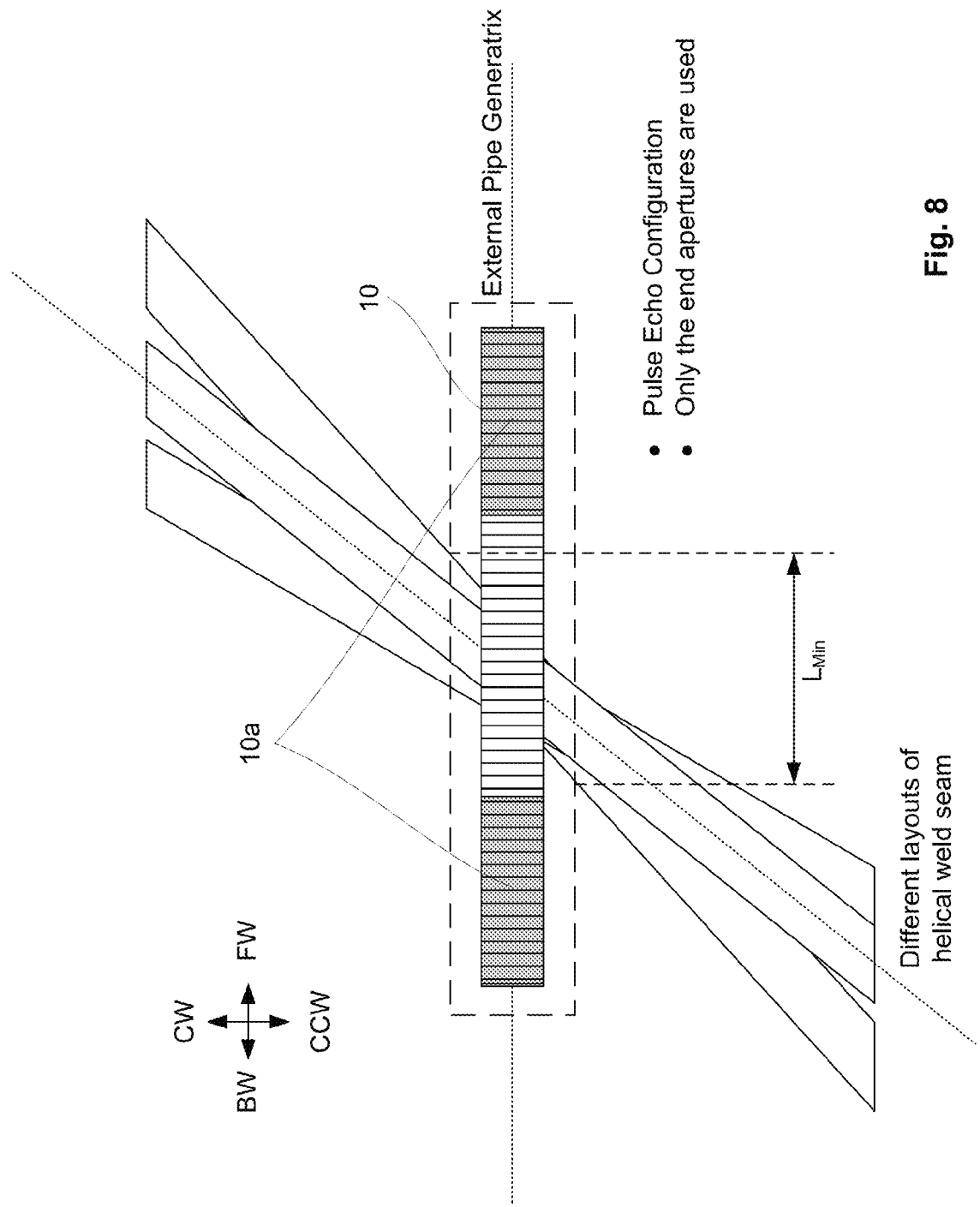
FIG. 8 is a more detailed schematic view of the PA probe for lamination flaw detection shown in FIG. 1

Referring to FIG. 1 and FIG. 8, inspection for lamination is provided to the Heat Affected Zone (HAZ) and the linear PA probe 10 is located on the top generatrix of the pipe to minimize the effect of the weld seam angle variation. The distance $L_{Min}$ is the minimum mechanical clearance required in the wear plate to accommodate the weld seam angle variation.

Again the variation of the weld bead width with wall thickness has to be taken into account to evaluate the distance $L_{Min}$. It could be necessary to have several $L_{Min}$ distance in function of the pipe size.

It should be noted that in the preferred embodiment shown in FIG. 8, only the ending apertures of probe 10 are used for the lamination inspection.

Alternatively, a configuration with two shorter PA probes or two UT probes instead of one long probe could be also considered for HAZ inspection. In this case, probes will be still mounted in the same probe holder but separated from a fixed distance less or equal to the minimum weld bead width $L_{Min}$. Then, aperture scanning is used to cover the HAZ Setting Up Operational Parameters Exemplary cases are herein used to provide more details on setting up operational parameters for using the presently disclosed PA system. The following procedure is preferably applied in order to set up the PA system correctly before each batch of inspection on test object with certain geometric parameters, such as diameter and thickness. It is done respectively for the probe configurations of 12*a* or 12*b* in FIG. 1 of the longitudinal flaw detections with P-E mode and tandem mode, and that of 14*a*-14*b* or 14*c*-14*d* in FIG. 1 of the transversal flaw detections with P-C mode.

A workable setup of the probe configurations in FIG. 1, either for the longitudinal flaw detections or for the transversal flaw detections, requires a set of predetermined parameters of water wedge, probe, beam steering and relative positions between the probe pair 14*a*-14*b* or 14*c*-14*d*, as a function of the pipe geometry, weld seam width and weld seam angle. The parameter setup process calculates this set of parameters, which is herein called "operational parameters".

A linear probe provides two electronically-controlled axes that are used to cancel certain mechanic movements of the probe. One axis is the aperture displacement along the probe and the other one is the angle steering ability. The extent for canceling mechanical movements of the longitudinal flaw detections and that of the transversal flaw detections need to be respectively analyzed by the parameter setup process.

Operational Parameters for Inspection of the Longitudinal Flaws in P-E Mode

As described above, probes 12*a* or 12*b* shown in FIG. 1 is configured to work in P-E mode for the ID and OD longitudinal notch detections. To save number of probes being used, the same set of probes works in tandem mode for the MW FBH detection (see FIG. 2). The MW FBH detection is required for larger pipe wall thickness, such as 12 mm or thicker.

To avoid making the space between the water wedge foot print and the weld seam edge to be too narrow, the beam skip number for the ID longitudinal notch detection is preferably set to 1.5, and that for the OD notch detection is set to 1.

The procedure for calculating the operational parameters for these detections is described in FIG. 9, which can be better understood with the help of FIGS. 10 and 11. A necessary condition for being able to define operational parameters is that the angle of the weld seam α in FIG. 11 is not undesirably small. The underlining reason is known to those skilled in the art because otherwise, the whole width of the weld seam cannot be efficiently covered by the probe arranged in parallel to pipe axis. This condition is valid because for the HSAW pipes the weld angle α is always greater than 50 deg.

Referring to FIG. 9, step 901 describes the necessary input parameters including:

Pipe parameters: the diameter, thickness, shear wave velocity and weld seam angle;

Probe parameters: aperture size and element pitch;

Water wedge parameters: the mechanic angle $\theta_L$, which is chosen by maximizing the inspectable weld width, and the water column;

For situations involving thicker wall pipes wherein an MW FBH to expected to inspect (see MW FBH in FIG. 10 or in FIG. 11, the flat bottom of the hole is defined by the intersection of mid-wall 1007 and mid-seam 1107), distance tolerance for returning beam 1004*f* at the probe 12*a* also needs to be determined.

In step 902, details of the parameter calculations for the case where there is not the MW FBH are described as follows.

Calculation of the steering angle that allows a normal incidence to the weld line;

Calculation of the beam skip points for longitudinal ID and OD notch inspections. The sound path is from 12*a*, 1002*a* to *d* and back to 12*a* as shown in FIG. 10;

Determination of the maximum inspectable weld width 1112$W_{B1}$ for ID and OD notch inspections;

Determination of the start and end aperture positions, 1103*a* and 1103*b* as shown in FIG. 10, according to the maximum inspectable weld width;

Determination of the probe length and the minimum numbers of elements required to perform the inspection.

As shown in FIG. 10, the sound path starts from an aperture in probe 12*a*, passes through skip points 1002*a* to *d*, and ends at the same aperture in probe 12*a*. An OD longitudinal notch is detected at skip point 1002*c* by corner trap and an ID longitudinal notch is detected at 1002*d* by corner trap. The inspectable weld width $W_{B1}$ shown in FIG. 11, which is defined by weld edges 1108*a* and 1108*b*, is determined by the criteria that weld bead area cannot support efficiently beam skips.

If a detection of the MW FBH is required (only for thick wall pipe), the procedure goes into the loop composed of steps 904-906. In step 904, the module sets the initial beam steering angle for transmission aperture 1005*a* of FIG. 11. Then in step 905, sound paths shown in FIGS. 10 & 11, 1105*a*, 1004*a*-1004*f* ending on aperture return 1105*b* are calculated. In step 906, it is checked if the beam crosses the probe 12*a* with the distance tolerance. If yes, the process is moved to step 907; otherwise it returns back to 904.

Since the detection of the MW FBH that uses totally less ID and OD skips in tandem mode, one has to make the related apertures approach the weld edge or the ID and OD skip points closer to the weld, and thus reduce the inspectable weld width. Therefore the inspectable weld width $W_{B1}$ obtained previously needs to be revised or reduced to the weld width $W_{B2}$, which is defined by weld edges 1107*a* and 1107*b* shown in FIG. 11. This is done in step 907.

Attention should be paid to the fact that the beam starting from aperture 1105a and arriving at aperture 1105b in FIG. 11 may not be in the same beam plane of the probe and therefore have an angular misalignment to any aperture in probe 12a receiving at any steering angle. This is explained in more detail in FIG. 12. The beam vector B arriving at probe 12a is not parallel to vector A that is generated by any aperture in the probe. There always exists a vector A belonging to the beam plane of probe 12a, whose direction the most approaches to that of vector B. For purpose of setting up parameters correctly, it is the direction of vector A that is chosen as the steering angle for receiving the beam 1004f in FIG. 10.

This angular misalignment could lower the reception sensitivity. However, after extensive calculations for the full diameter range of the HSAW pipe from 16" to 100", it was observed that the misaligned angle is never greater than 2 deg, indeed a very small angle relative to the beam divergent angle of 2.25 MHz probes.

It should be noted that this approach of using vector A approximating vector B representing another important novel aspect of the present disclosure, allowing a single probe, such as 12a or 12b, to inspect the longitudinal flaws, and in the transversal flaw inspection allowing a single pair of probes, such as 14a and 14b or 14c and 14d, to inspect both OD and ID notches.

It should be understood that transmission aperture 1105a and reception aperture 1105b in FIG. 11 can be interchanged for the MW FBH detection without affecting the parameter setup result.

Finally, in step 908, the parameters for the configuration of probe 12a or 12b in FIG. 1 are provided in output as follows.
Beam steering angle for ID and OD notch inspection and aperture positions on probe 110112a
Distance between probe edge and center of weld seam $D_L DL$
Maximum inspectable weld width $W_{B1} B1112$
Minimum required probe element quantity
All refraction angles
If there is an MW FBH to be detected, the results from the routine 904-907 for this scenario is given for the following:
Beam steering angle of transmission for MW FBH detection and the refraction angle;
Beam steering angle of reception for the FBH detection and refraction angle;
Revised maximum inspectable weld width $W_{B2} B$;
Transmission and reception aperture positions 1105a and 1105b.

As a result, referring to the exemplary ray tracing or operational parameter setup in FIGS. 10 and 11, if weld angle α changes, without probe movement, the beam steering of the phased-array probe allows a perpendicular beam incidence to the weld seam of angle α, while the linear scan apertures from 1103a to 1103b sufficiently cover a certain weld width for both ID and OD notch detections at a constant refraction angle; similarly the coverage of the MW FBH can make use of the angle steering of the two apertures 1105a and 1105b combining with a translation of the two apertures. If the wall thickness varies but there is still no geometric conflict between the water wedge foot print and the weld edge, without probe movement, the apertures can be translated, in probe 12a along the pipe axis, nearer or further from the weld (a thickness change doesn't necessarily require a change of the steering angles).

Figure 13:
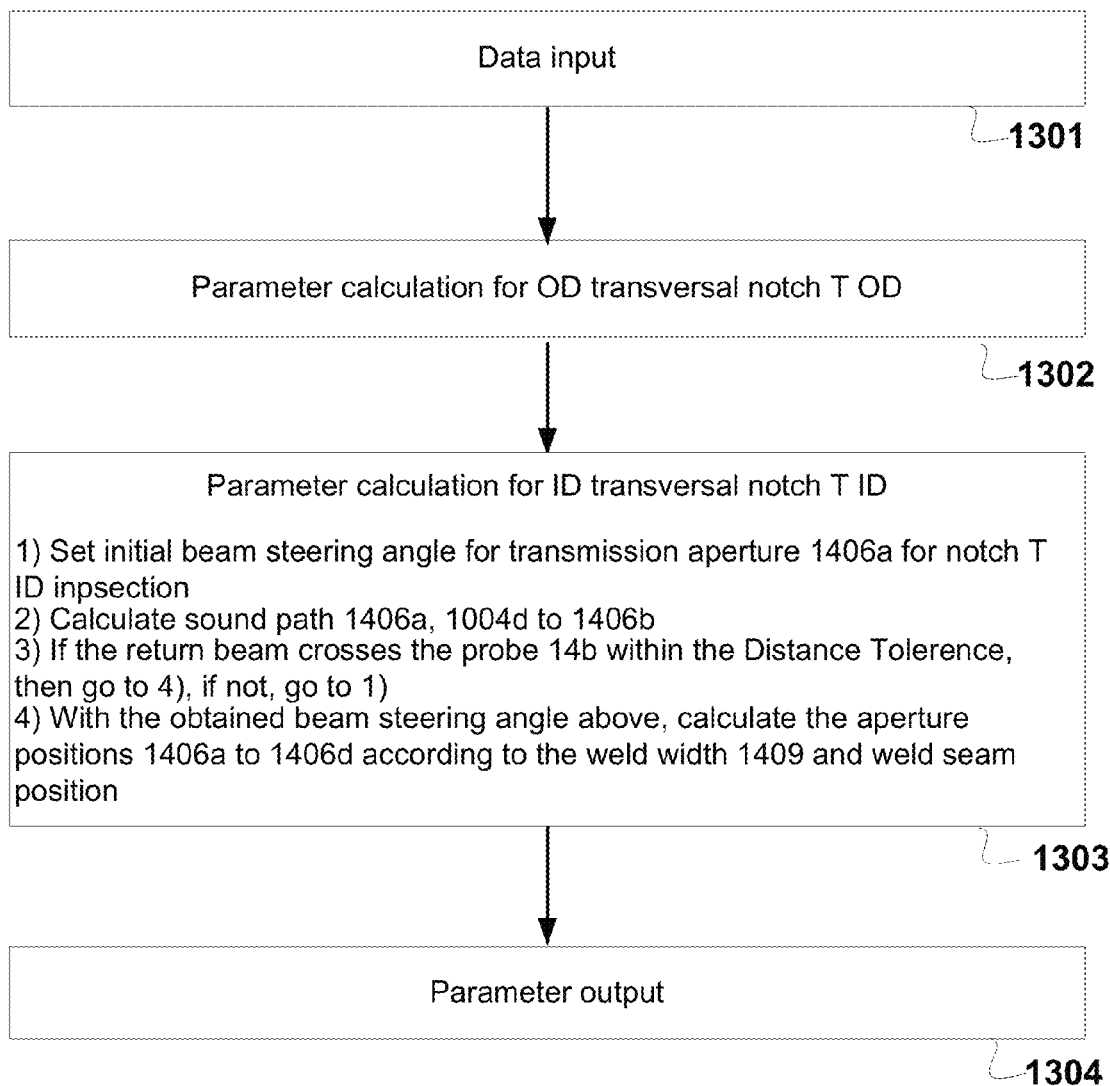
FIG. 13 is a flow chart of the ray tracing for the transversal notch detections shown in FIGS. 4 and 5, and FIGS. 6 and 7.
Figure 14A:
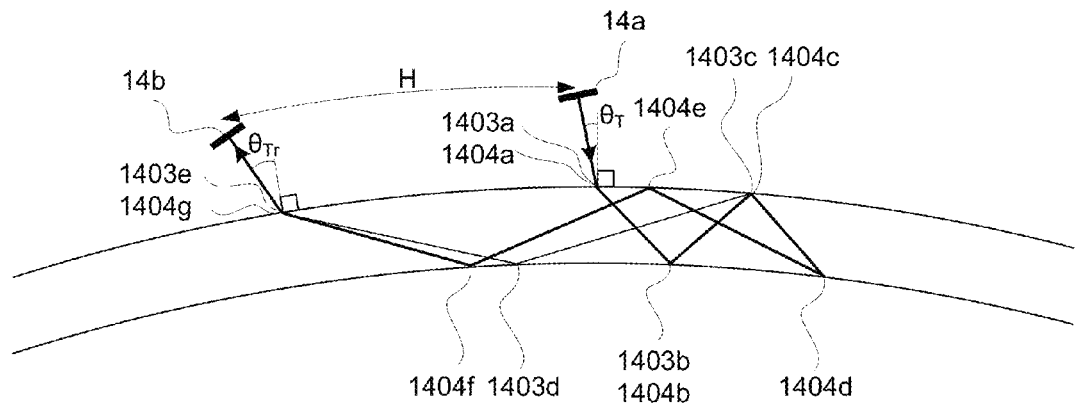
FIGS. 14a and 14b are an exemplary ray tracing for the transversal notch detections shown in FIGS. 4 and 5.
Figure 14B:
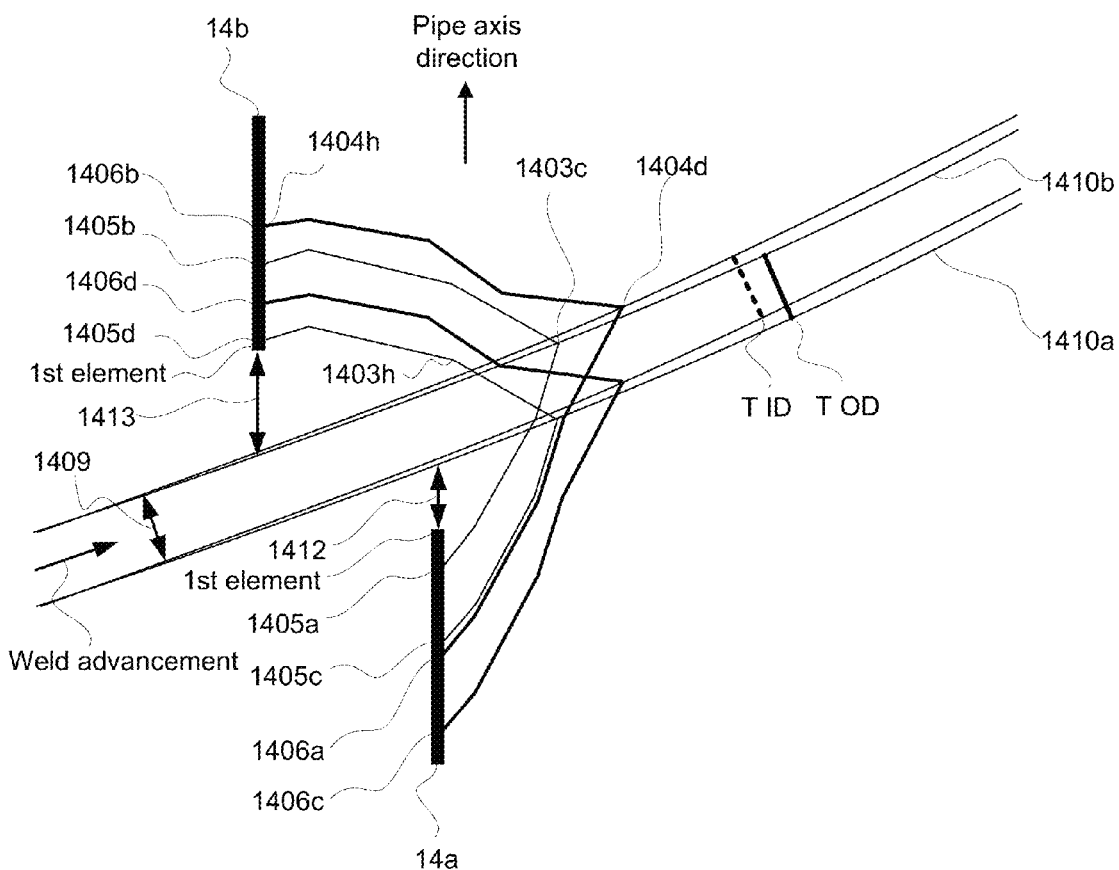

Operational Parameter Setup for the Inspection of the Transversal Flaws in P-C Mode As described above, the pair of probes shown as 14a-14b or 14c-14d in FIG. 1, is configured to work in pitch-catch mode for detections of both ID and OD transversal notches, T OD and T ID in FIG. 14b, respectively. The procedure as shown in FIG. 13 for calculating the operational parameters needed to setup the PA system correctly is described as follows, which can be better understood with the help of FIGS. 14a and 14b.

Referring to FIG. 13, in step 1301, input is provided to the PA system for the following testing condition parameters:
Pipe parameters: the diameter, thickness, shear wave velocity and weld seam angle;
Probe parameters: the aperture size and element pitch;
Water wedge parameters for transmitter 14a: the water wedge angle $\theta_T$, which is chosen for maximizing the inspectable weld width, water column and wave velocity in water;
Water wedge parameters for receiver 14b: the water column;
Beam separation angle, at the OD transversal notch detection, between the incident beam and the reflected beam. This angle is chosen by maximizing the inspectable weld width.
Limit conditions: the maximum refraction angle (e.g.: <70 deg), maximum electric steering angle (e.g.: <24 deg) and maximum water wedge angle $\theta_{T_r}$ for receiver 14b (e.g.: <22 deg).
Distance Tolerance for the returning beam at receiver 14b for ID notch detection.

There are 2 steps of the parameter setup process respectively for the OD transversal notch detection and the ID transversal notch detection, by using a same pair of probes 14a-14b or 14c-14d in FIG. 1.

Step 1302 describes the calculation steps for obtaining the parameters of the OD transversal notch T OD detection. There isn't any approximation in this step in terms of ray tracing. Particularly, the maximum inspectable weld width 1409 defined by weld edges shown as 1410a and 1410b on external surface is obtained. Any part of the external transversal notch T OD moving with the weld seam is detected by meeting the beam skip point 1403c of one of the P-C mode apertures between 1405a (1405b) and 1405c (1405d).

More specifically, step 1302 includes the calculation for the following:
Calculation of steering angles of transmitter aperture 1405a and receiver aperture 1405b for pitch-catch mode and the mechanical angle of transmitter 14a, by maximizing the inspectable weld width (the same for ID and OD)
After the above calculations, in FIG. 14(a), the position of receiver 14b and that of the inspectable weld width with respect to the position of transmitter 14a are obtained. The mechanical angle of receiver 14b is obtained. Skip points 1403a to 1403e are calculated at the same time.
Determination of the linear scan range that ends at the position of transmitter aperture 1405c. If skip point 1403h is in the weld, the maximum inspectable weld width 1409 is reduced accordingly.

In step 1303, referring to FIG. 14b, based on the non-electronically controllable parameters obtained above, i.e.: the relative positions among the two probes 14a, 14b and the weld, and the water wedge angle of receiver 14b, the beam 1404h returning from ID transversal notch T ID is calculated. The notch moving with the weld seam is detected at ID skip point 1404d, by varying the aperture position and the steering angles in both transmission aperture 1406a and reception aperture 1406b (see also sound path 14a, 1404a-g to 14b in FIG. 14(a)). The distance error of the returning beam arriving at reception aperture 1406b should be within the input Distance Tolerance. Then the scanning range (i.e.: the positions of apertures 1406c and 1406d) are calculated according to the maximum inspectable weld width 1409.

Attention should be paid to the fact that the beam starting from aperture 1406a and arriving at probe 14b may not be in the beam plane of probe 14b and therefore may have a certain angular misalignment to any aperture in probe 14b receiving at any steering angle. This is explained in FIG. 12. The beam vector B arriving at probe 14b is not parallel to vector A that is generated by any aperture in the probe. There exists always a vector A belonging to the beam plane of probe 14b, whose direction the most approaches to that of vector B. For the ray tracing or parameter setup technique herein disclosed, it is the direction of this vector A that is chosen as the steering angle for receiving the beam 1404h in FIG. 14(b).

This angular misalignment could lower the reception sensitivity. However, after extensive calculations for the full diameter range of the HSAW pipe from 16" to 100", it was observed that the misaligned angle is never greater than 2 deg, indeed a very small angle relative to the beam divergent angle of 2.25 MHz probes.

Referring back to FIG. 14b, it should be understood that transmission aperture 1406a and reception aperture 1406b are interchangeable without affecting the operational parameter result for the ID transversal notch detection.

It should also be understood that the position and the mechanic angle of reception probe 14b can also be obtained first by detecting the ID transversal notch without any approximation in terms of ray tracing during operational parameter setup, and then the receiving steering angle of probe 14b for the transversal OD notch detection is obtained by minimizing the angular misalignment.

Step 1303 is summarized as follows.
Calculation of the steering angles of transmitter aperture 1406a and receiver aperture 1406b for pitch-catch mode by minimizing the distance between receiver 1402b and the received beam through point 1404g, whose sound path is from 1406a to 1406b reflected by the end of notch 1408T ID at skip point 1404d;
If the error is within the Distance Tolerance, the calculation stops.

Finally, in step 1304, the parameters for the configuration of probe pair 14a-14b or 14c-14d in FIG. 1 are output.

Referring to the exemplar parameter setup result in FIG. 14(b), without a probe movement in directions other than along the weld seam, the linear scan covers a certain weld width for both ID and OD notch detections at a constant refraction angle. The feature can compensate a certain mechanic movement of the probes along the pipe axis, as long as there isn't a geometric conflict between the water wedge foot print and the OD weld edge. However, due to the P-C mode, a change of the weld angle a or a change of wall thickness leads to repositioning transmission probe 14a and reception probe 14b in the pipe circumferential direction.

Guided by the above teachings of the unique understanding and novel treatment of the operational parameter setup procedure, specifically to the probe configuration as presently disclosed, one skilled in the art should obtain the detailed calculation of the set of operational parameters. To summarize the teachings on setting up operational parameters include the understanding and achieving the desired coverage and resolution for both ID and OD for the entire width of the weld seam without requiring probes mechanical adjustment by using a combination of sound paths, skip points, mechanical angle and steering angles and the way of approximation.

The need for mechanically adjusted probe angle can be alternatively eliminated by the use of matrix PA probe for which electronic steering angle can be obtained in all directions. Otherwise, the use of such probe for HSAW inspection would be within the scope of the invention.

Figure 12:
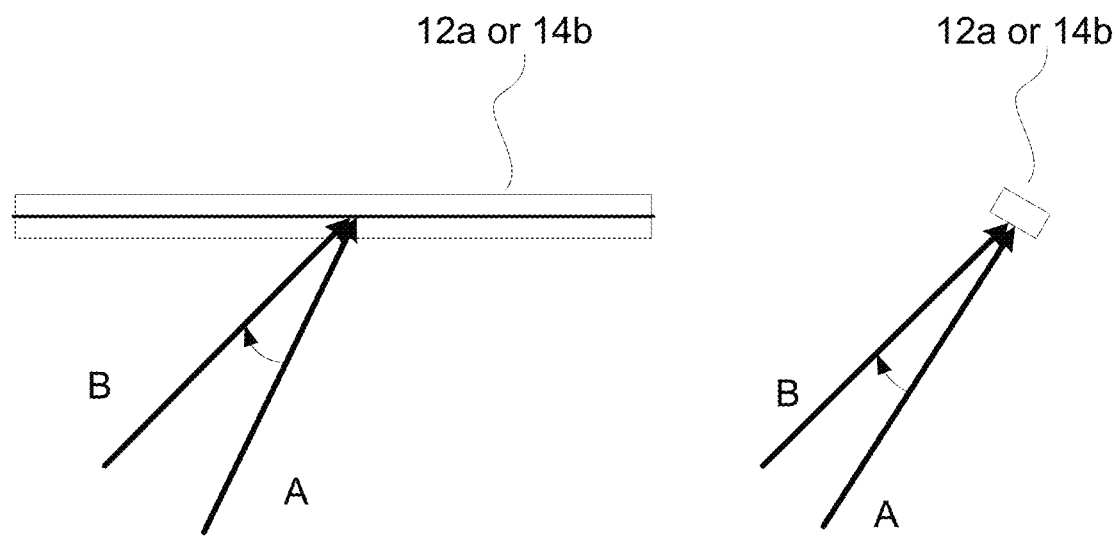
FIG. 12 is an exhibition of angular misalignment between a reception vector A in the beam plane of the probe and a returning beam B arriving at the probe.

As described above, FIG. 1 is a schematic view of the configuration of all PA probes devised in the phased array HSAW system in order to achieve a full scan in one pass according to the present disclosure. FIG. 2 is a schematic view of a pair of the PA probes 12a or 12b for longitudinal flaw detections shown in FIG. 1. The longitudinal flaws include longitudinal ID notches in different weld width locations, longitudinal OD notches in different weld width locations, a thru hole and a MW FBH at the center of the weld. FIG. 3 is a schematic view of the linear scan across the weld seam with the PA probe 12a and 12b for longitudinal ID and OD notch detections. The apertures 20a of probes 12a and 12b are exhibited to work together in P-C mode to achieve coupling check through point 301. FIG. 4 is a schematic view of two pairs of PA probes in P-C mode, 14a and 14b or 14c and 14d, for transversal weld seam OD detections shown in FIG. 1. FIG. 5 is a schematic view of the linear scan across the weld seam with two pairs of PA probes in P-C mode for transversal OD notches detection. FIG. 6 is a detailed schematic view of two pairs of PA probes in P-C mode, 14a and 14b or 14c and 14d, for transversal ID notches detection shown in FIG. 1. FIG. 7 is a more detailed schematic view of the linear scan across the weld seam with two pairs of PA probes in P-C mode for transversal ID notches detection. The aperture 401d of probe 14b and aperture 401d-2 of probe 14d work together in P-C mode to achieve coupling check through point 701. FIG. 8 is a more detailed schematic view of the PA probe 10 for lamination flaw detection shown in FIG. 1. FIG. 9 is a flow chart of the ray tracing for the longitudinal flaw detections shown in FIGS. 2 and 3. FIG. 10 is an end view of an exemplary ray tracing for the longitudinal flaw detections shown by FIGS. 2 and 3. One beam for the OD and the ID notch detections and one beam for the MW FBH detection is shown. FIG. 11 is a top view of an exemplary ray tracing for the longitudinal flaw detections shown by FIGS. 2 and 3. FIG. 12 is an exhibition of angular misalignment between a reception vector A in the beam plane of the probe and a returning beam B arriving at the probe. FIG. 13 is a flow chart of the ray tracing for the transversal notch detections shown in FIGS. 4 and 5, and FIGS. 6 and 7. FIGS. 14a and 14b are an exemplary ray tracing for the transversal notch detections shown in FIGS. 4 and 5.

What is claimed is:

1. A method of conducting an ultrasonic inspection inspecting a helical weld seam of a pipe using an ultrasonic phased array system having a set of phased array probes, the pipe having an inner and an outer surface, and with each of the probes having two ends and a probe active axis, and each of the probes is placed on the outer surface of the pipe, arranged with its respective active axis in alignment with the longitudinal axial line of the pipe, and each of the probes has plurality of apertures, and the set of the probes collectively having a scanning movement along and immediately adjacent to the helical weld seam, wherein the positions of the probes remain substantially fixed relative to each other,
 the method comprises the steps of:
  a. using at least a first probe placed over the weld seam and overlapping the axial line of the pipe for inspecting lamination defects located at the weld seam;
  b. using at least a second pair of linear probes placed on opposite sides of the weld seam in a fashion that allows their focal laws applied facing each other and focused on the same general area of the weld seam simultaneously, for fully inspecting standardly known types of longitudinal defects located at the weld seam;

c. using at least a third and a fourth pairs of linear probes respectively placed on opposite sides of the weld seam in a fashion that allows their respective pairs of focal laws applied facing each other and focused on the same respective general area of the weld seam simultaneously, for inspecting standardly known transversal defects located at the weld seam, and;

wherein inspection is conducted with a single pass of the scanning movement over the helical weld seam.

2. The method of claim 1 wherein the set of probes collectively are moveable only along the weld seam, and are substantially fixed in any directions other than along the weld seam.

3. The method of claim 1 wherein for each correspondingly working pairs of apertures, the distance between the first element of each aperture and the center of the weld seam is equal.

4. The method of claim 1, wherein only those of the apertures closer to two ends of the first probe are active during the inspection.

5. The method of claim 1, wherein some of the apertures of the second pair of probes are operated in pulse echo mode, and are configured using a combination of aperture scanning, mechanical angle and steering angles of the respective probe for inspecting longitudinal notches possibly located at any spot of the weld seam, including close to both the inner and outer surfaces, across the full width, and across the full thickness of the weld seam.

6. The method of claim 5, wherein each of the second pair of probes is operated in pulse echo mode to inspect one side of the longitudinal notches.

7. The method of claim 1, wherein some of the apertures of the second pair of probes are operated in tandem mode and can be configured for inspecting both sides of flat-bottom-holes in the mid-wall of the pipe.

8. The method of claim 1, wherein a predetermined group of the apertures of the third pair and forth pair of probes are operated in pitch-catch mode using a combination of aperture scanning, mechanical angle and steering angles of the respective probe for inspecting transversal notches possibly located at any spot of the weld seam, including spot close to both the inner and outer surfaces and across the full width of the weld seam.

9. The method of claim 8, the third pair and the forth pair of probes are used simultaneously to inspect the transversal defects clock-wisely and counter-clock-wisely simultaneously, respectively.

10. The method of claim 8, wherein aperture scanning is conducted in such a way that the apertures in corresponding pair of probes are sequentially paired for pitch-catch operation to scan the full width and full thickness of the weld seam for transversal defects, including both inner and outer surfaces of the weld seam.

11. The method of claim 1 further comprising a step of coupling check, by which a testing focal law applied from one aperture of one of the pairs of probes on the pipe, is checked on an expected receiving aperture of the corresponding probe of the respective pair of probes.

12. The method of claim 1, wherein the step of using the second pair of probes further comprises a second setup procedure for setting up operational parameters, the second setup procedure including steps of:

a. analyzing a sound path of an aperture of one of the second pair of probes originated from an aperture on one end of one of the second pair of probe, reaching a farthest side of the weld seam on which one of the defects is possibly located, with a returning beam ending at a reception aperture of the probe, the sound path involves the usage of at least one mechanical angle and steering angles;

b. evaluating whether the returning beam is within a predetermined distance tolerance;

c. calculating a maximum inspectable weld width which should be larger than a predetermined weld width required to be inspected;

d. determining the operational parameters including the respective positions of the second pair of probes, mechanical angle, steering angles of the apertures used for inspecting the longitudinal defects.

13. The method of claim 1, wherein the step of using the third pair of probe further comprises a third setup procedure for setting up operational parameters, the third setup procedure including steps of:

a. analyzing a sound path originated from an aperture on one end of one of the third or the forth pair of probes, reaching a farthest side of the weld seam on which one of the transversal defects is possibly located, with a returning beam ending at a reception aperture of the corresponding probe of the corresponding pair, the sound path involves the usage of at least one mechanical angle and steering angles;

b. evaluating whether the returning beam is within a predetermined distance tolerance;

c. calculating a maximum inspectable weld width which should be larger than a predetermined weld width required to be inspected;

d. determining the operational parameters including the respective positions of the third or forth pair of probes, mechanical angle, steering angles of the apertures used for inspecting the transversal defects.

14. The system of claim 13, wherein the transversal operational parameters module is configured to execute the following tasks:

a. calculating a specific sound path originated from an aperture on one end of one of the third pair of probes, reaching a farthest side of the weld seam on which one of the transversal defects is possibly located, with a returning beam ending at a reception aperture of the probe, the sound path involves the usage of at least one mechanical angle and steering angles;

b. evaluating whether the returning beam is within a predetermined distance tolerance;

c. calculating a maximum inspectable weld width which should be larger than a predetermined weld width as required to be inspected;

d. determining the operational parameters including the respective positions of the third or fourth pair of probes, mechanical angle, steering angles of the apertures used for inspecting the transversal defects.

15. A phased array system configured for conducting an ultrasonic inspection inspecting a helical weld seam of a pipe, the pipe having an inner and an outer surface, the system including and electronically coupled with a set of phased array probes, and with each of the probes having two ends and a probe active axis, and each of the probes is placed on the outer surface of the pipe, arranged with its respective active axis in alignment with the longitudinal axial line of the pipe, and each of the probes has plurality of apertures, and the set of the probes collectively having a scanning movement along and immediately adjacent to the helical weld seam, wherein the positions of the probes remain substantially fixed relative to each other, the set of probes comprises:
- a. at least a first linear probe placed over the weld seam and overlapping the axial line of the pipe for inspecting lamination located at the weld seam;
- b. at least a second pair linear probes placed on opposite sides of the weld seam in a manner that allows their focal laws applied facing to each other and focused on the same general area of the weld seam simultaneously, for fully inspecting standardly known types of longitudinal defects located at the weld seam,
- c. at least a third and fourth pairs of linear probes respectively placed on opposite sides of the weld seam in a fashion that allows their respective pairs of focal laws applied facing each other and focused on the same respective general area of the weld seam simultaneously, for inspecting standardly known transversal defects located at the weld seam, and,
- d. the phased array system further comprises at least a longitudinal operational parameter module and at least a transversal operational parameter module which configure the system for inspecting the full-width of weld seam at both the inner and outer surfaces with one pass of the scanning movement.

16. The system of claim 15, wherein the first linear probe is operated in pulse-echo mode and only those of apertures closer to two ends of the first probe are active during the inspection.

17. The system of claim 15, wherein some of the apertures of the second pair of probes are operated in pulse echo mode, and are configured using a combination of aperture scanning, mechanical angle and steering angles of the respective probe for inspecting longitudinal notches located at a location possibly any spot of the weld seam, including spots close to both the inner and outer surfaces, across the full width, and across the full thickness of the weld seam, wherein each of the second pair of probes is operated to inspect one side of the longitudinal notches.

18. The system of claim 15, wherein some of the apertures of the second pair of probes are operated in tandem mode and can be configured for inspecting both sides of flat-bottom-holes in the mid-wall of the pipe.

19. The system of claim 15, wherein a predetermined group of the apertures of the third pair and forth pair of probes are operated in pitch-catch mode using a combination of aperture scanning, mechanical angle and steering angles of the respective probe for inspecting transversal notches possibly located at any spot of the weld seam, including close to both the inner and outer surfaces and across the full width of the weld seam.

20. The system of claim 15, wherein the third pair and the fourth pair of probes are used simultaneously to inspect the transversal defects clock-wisely and counter-clock-wisely simultaneously, respectively.

21. The system of claim 15, wherein aperture scanning is conducted in such a way that the apertures in corresponding pair of probes are sequentially paired for pitch-catch operation to scan the full width and full thickness of the weld seam for transversal defects at both inner and outer surfaces.

22. The system of claim 15, wherein the longitudinal operational parameters module is configured to execute the following tasks:
- a. calculating a specific sound path originated from an aperture on one end of one of the second pair of probe, reaching a farthest side of the weld seam on which one of the defects is possibly located, with a returning beam ending at a reception aperture of the probe, the sound path involves the usage of at least one mechanical angle and steering angles;
- b. evaluating whether the returning beam is within a predetermined distance tolerance;
- c. calculating a maximum inspectable weld width which should be larger than a predetermined weld width required to be inspected;
- d. determining the operational parameters including the respective positions of the second pair of probes, mechanical angle, steering angles of the apertures used for inspecting the longitudinal defects.

* * * * *